US010383965B2

(12) United States Patent
Dombrowsky

(10) Patent No.: US 10,383,965 B2
(45) Date of Patent: Aug. 20, 2019

(54) ULTRAVIOLET LIGHT-STERILIZED AND ILLUMINATING CASTER WHEEL SETS

(71) Applicant: HealthierStep, Inc., Oyster Bay, NY (US)

(72) Inventor: Rachel Dombrowsky, Hewlett, NY (US)

(73) Assignee: Harbor Innovations, LLC, Oyster Bay, NY (US)

( * ) Notice: Subject to any disclaimer, the term of this patent is extended or adjusted under 35 U.S.C. 154(b) by 0 days.

(21) Appl. No.: 15/900,195

(22) Filed: Feb. 20, 2018

(65) Prior Publication Data
US 2018/0272014 A1 Sep. 27, 2018

Related U.S. Application Data

(60) Provisional application No. 62/474,244, filed on Mar. 21, 2017.

(51) Int. Cl.
A61L 2/10 (2006.01)
A61L 2/24 (2006.01)
(Continued)

(52) U.S. Cl.
CPC .............. A61L 2/10 (2013.01); A61G 5/10 (2013.01); A61L 2/24 (2013.01); B23P 19/04 (2013.01);
(Continued)

(58) Field of Classification Search
USPC ..................... 250/455.11; 16/35 R
See application file for complete search history.

(56) References Cited

U.S. PATENT DOCUMENTS 7,712,184 B1  5/2010 Lewis et al.
9,615,983 B2 * 4/2017 Stryker ................ A61G 7/05
2014/0265181 A1 9/2014 Lambarth et al.

FOREIGN PATENT DOCUMENTS

WO 2012035295 A1 3/2012
WO 2017039546 A1 3/2017

OTHER PUBLICATIONS

PCT International Search Report dated Jun. 29, 2018 for Application No. PCT/US2018/023290.
(Continued)

Primary Examiner — Phillip A Johnston
(74) Attorney, Agent, or Firm — Carter, DeLuca & Farrell LLP; George Likourezos

(57) ABSTRACT

A caster wheel assembly includes a swivel frame and a caster wheel rotatably coupled to the swivel frame via an axle. The swivel frame can include a rotatable shaft enabling rotation of the wheel and at least one light emitting diode (LED) disposed on a surface of the swivel frame to at least partially illuminate ambient surroundings. The LED may be an ultraviolet (UV) LED disposed on the surface of the swivel frame to interface a portion of the caster wheel thereby enabling UV light emitting from the LED to sterilize pathogens colonizing the caster wheel. The LED may be disposed on an external surface of the swivel frame to at least partially illuminate ambient surroundings. Upon an adjustable predetermined time or distance of motion, the wheel may be braked for ultraviolet light to sterilize pathogens colonizing the caster wheel and released following an adjustable predetermined time.

20 Claims, 15 Drawing Sheets

(51) Int. Cl.
*B60B 33/00* (2006.01)
*B23P 19/04* (2006.01)
*A61G 5/10* (2006.01)
*A61G 1/02* (2006.01)

(52) U.S. Cl.
CPC .............. *B60B 33/006* (2013.01); *A61G 1/02* (2013.01); *A61L 2202/14* (2013.01); *A61L 2202/16* (2013.01); *A61L 2202/20* (2013.01)

(56) References Cited

OTHER PUBLICATIONS

Service Caster, Medical Lab & Hospital Equipment Casters IV Pole Wheels, http://shop.servicecaster.com/medical-hospital-casters->s/2036.htm?gclid=CMuPp8XfidICFZiCswod3iUOvQ, printed Jun. 29, 2018 (3 pages).
Kim et al., "Sterilization of Pathogenic Bacteria Using Titanium Dioxide Photocatalyst", https://www.researchgate.net/publication/267773590_Sterilization_of_Pathogenic_B <http://www.researchgate.net/publication/267773590_Sterilization_of_Pathogenic_Bacteria_Using_Titanium_Dioxide_Photocatalyst, printed Jun. 29, 2018 (9 pages).
Testco Electronic Component Distribution, <http://www.testco-inc.com/Iedex?_vsrefdom=adwords&gclid=Cj0KCQiAv_HSBRCkARIsAGaSsrDe9_0Yq_IARg17fYrkzH-RNPyfDO3h2Z2SGD57QGo-ygdsF0uXhMaAh0oEALw_wcB>, printed Jun. 27, 2018 (8 pages).
Blenkham, "Potential compromise of hospital hygiene by clinical waste carts", Journal of Hospital Infection, vol. 63, Issue 4, pp. 423-427 (Aug. 2006), Abstract (3 pages).
Scholar Google Search, <https://scholar.google.com/scholar?hl=en&as_sdt=0%2C33&q=hospital+caster+wheel+surfaces+pathology&btnG>, printed Jun. 27, 2018 (2 pages).
Patient safety through evidence-based design and innovative technology, Stryker Patient Care, <https://patientcare.stryker.com/en/products/beds>, printed Jun. 27, 2018 (7 pages).
Hospital Beds & Long Term Care Beds, <https://www.hill-rom.com/international/Products/Products-by-Category/hospital-beds-long-term-care-beds/>, printed Jun. 27, 2018 (3 pages).
Allen Medical, <https://www.allenmedical.com/>, printed Jun. 27, 2018 (2 pages).

\* cited by examiner

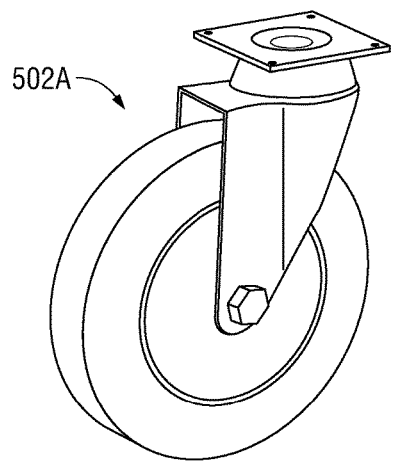
FIG. 2A
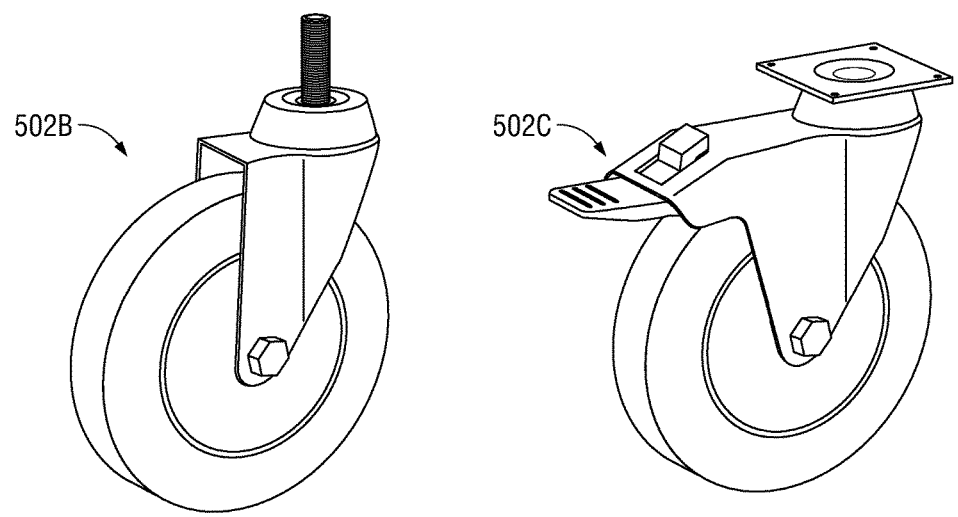
FIG. 2B
FIG. 2C

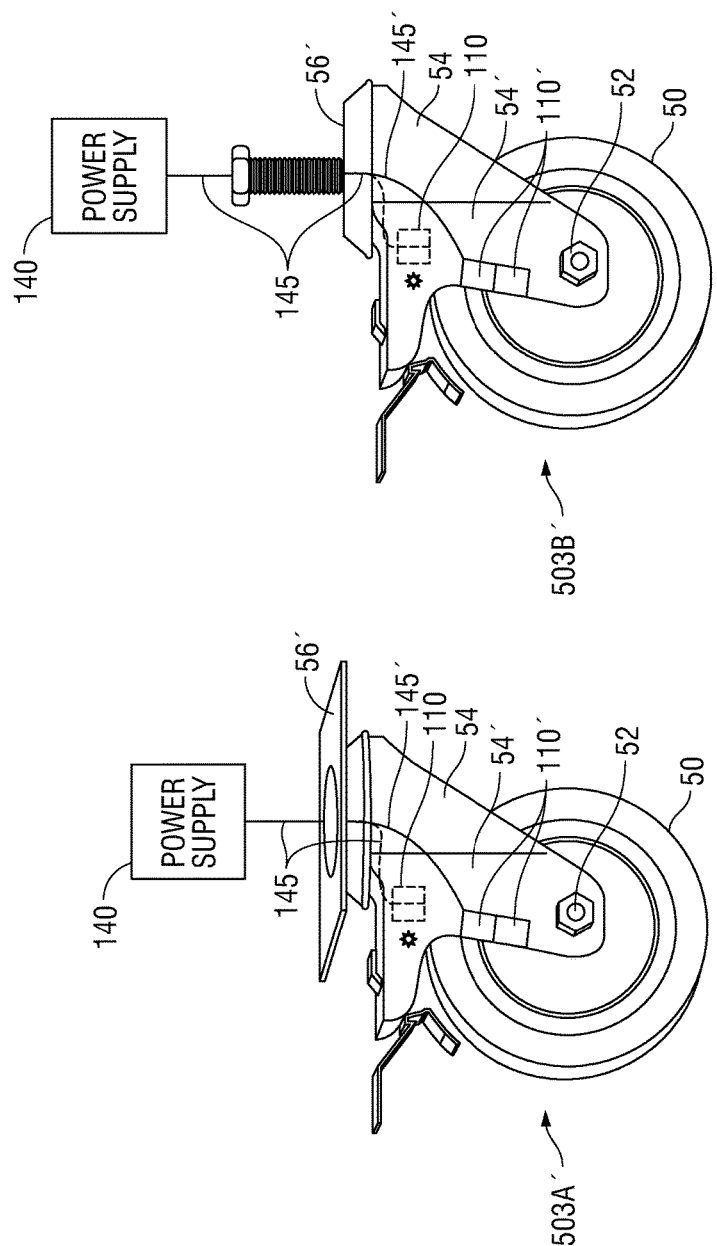

ULTRAVIOLET LIGHT-STERILIZED AND ILLUMINATING CASTER WHEEL SETS

CROSS-REFERENCE TO RELATED APPLICATIONS

This application claims priority to, and the benefit of, U.S. Provisional Patent Application No. 62/474,244 by Rachel Dombrowsky et al. entitled "ULTRAVIOLET LIGHT-STERILIZED CASTER WHEEL SETS", filed on Mar. 21, 2017, the entire contents of which are incorporated herein by reference.

BACKGROUND

A caster is defined in the Merriam-Webster dictionary to be any of a set of wheels or rotating balls mounted in a swivel frame and used for the support and movement of furniture, trucks, and portable equipment.

In hospital, medical, nursing home, rehabilitation facilities and some portions of assisted living facilities and the like, and including pharmaceutical manufacturing facilities, medical equipment, diagnostic devices and supplies, etc., are mounted on carts that include casters for transport. Similarly, patients are transported on beds that are mounted on casters.

Such carts and beds must often be transported by staff into dimly lit areas such as occur during evening hours or during power outages.

In addition, regardless of the ambient lighting conditions within a facility, pathogens including viruses and bacteria may accumulate and colonize on the surfaces of the wheels of the caster sets in such equipment and be spread by the transport and movement of such equipment throughout such facilities.

As a result, pathogens including viruses and bacteria may accumulate and colonize on the surfaces of the wheels of the caster sets in such equipment and be spread by the transport and movement of such equipment throughout such facilities.

SUMMARY

The present disclosure describes significant and non-obvious technical features to address needs for illumination and ultraviolet sterilization of pathogens in the aforementioned buildings and facilities by disclosing a lighting assembly that includes at least one enclosure defining an internal volume configured and disposed to receive in the internal volume a portion of at least one caster wheel that includes a rotatable shaft enabling rotation of the at least one caster wheel; at least one structural mounting member configured and disposed to attach the one or more enclosures to the rotatable shaft; and at least one ultraviolet (UV) light-emitting diode (LED) disposed in the internal volume of the one or more enclosures to interface the portion of the caster wheel thereby enabling UV light emitting from the LED to illuminate the portion of the caster wheel to enable sterilization of pathogens colonizing at least a portion of the portion of the caster wheel received in the internal volume and to at least partially illuminate ambient surroundings. The one or more enclosures, the one or more structural mounting members and the one or more UV LEDs defining thereby a caster enclosure and UV LED sterilization and illumination lighting assembly.

Alternatively, one or more LEDs are disposed on an external surface of the one or more enclosures to at least partially illuminate ambient surroundings such that the one or more enclosures, the one or more structural mounting members, and the one or more LEDs define thereby a caster enclosure and LED illumination lighting assembly.

Alternatively, combinations of the one or more enclosures, the one or more structural mounting members and the one or more UV LEDs define thereby a caster enclosure and UV LED sterilization and illumination lighting assembly and the one or more enclosures, the one or more structural mounting members, and the one or more LEDs define thereby a caster enclosure and LED illumination lighting assembly.

In an aspect, the lighting assembly may further include an electrical power supply in electrical communication with the one or more LEDs.

In an aspect, the lighting assembly may further include a motion detector and timer switch; an electrical braking component configured to enable braking of the one or more caster wheels; and an electrical power supply in electrical communication with the motion detector and timer switch and the electrical braking component and with the one or more LEDs disposed on a surface of the one or more enclosures.

The one or more LEDs disposed on a surface of the one or more enclosures is at least one ultraviolet (UV) light emitting diode (LED) disposed on the surface of the one or more enclosures to interface a portion of the caster wheel thereby enabling UV light emitting from the LED to illuminate the portion of the caster wheel to enable sterilization of pathogens colonizing at least the portion of the caster wheel wherein, upon a predetermined time of motion or distance of motion of the caster wheel assembly, the motion detector and timer switch transmit a signal to the electrical braking component to halt motion of, or brake, the caster wheel assembly and to electrically activate the one or more ultraviolet (UV) light emitting diodes (LED) to illuminate the portion of the caster wheel to enable sterilization of pathogens colonizing at least the portion of the caster wheel.

In a further aspect, upon expiration of a predetermined activation time of at least one ultraviolet (UV) light emitting diode (LED), the motion detector and timer switch transmit a signal to the electrical braking component to enable motion of the caster wheel and to deactivate the one or more ultraviolet (UV) light emitting diodes (LED).

The present disclosure relates also to a caster wheel assembly that includes a swivel frame configured to receive at least one caster wheel; a wheel rotatably coupled to the swivel frame via an axle to define thereby a caster wheel assembly, wherein the swivel frame includes, or is configured to enable coupling to, a rotatable shaft enabling rotation of the at least one caster wheel; and at least one light emitting diode (LED) disposed on a surface of the swivel frame to at least partially illuminate ambient surroundings.

In a further aspect, the at least one LED disposed on a surface of the swivel frame is at least one ultraviolet (UV) light emitting diode (LED) disposed on the surface of the swivel frame to interface a portion of the caster wheel thereby enabling UV light emitting from the LED to illuminate the portion of the caster wheel to enable sterilization of pathogens colonizing at least the portion of the at least one caster wheel.

In one aspect, the one or more light emitting diodes (LED) is disposed on an external surface of the swivel frame to at least partially illuminate ambient surroundings.

In an aspect, an electrical power supply is in electrical communication with the one or more LEDs.

In another aspect, the caster wheel assembly further includes: a motion detector and timer switch; an electrical braking component configured to enable braking of the caster wheel; and an electrical power supply in electrical communication with the motion detector and timer switch and the electrical braking component and with the one or more ultraviolet (UV) light emitting diodes (LED) disposed on a surface of the swivel frame, Upon a predetermined time of motion or distance of motion of the caster wheel assembly, the motion detector and timer switch transmit a signal to the electrical braking component to brake, or halt, motion of the caster wheel assembly and to electrically activate the one or more ultraviolet (UV) light emitting diodes (LED) to illuminate the portion of the caster wheel to enable sterilization of pathogens colonizing at least the portion of the one or more caster wheels.

In a further aspect, upon expiration of a predetermined activation time of the one or more ultraviolet (UV) light emitting diodes (LED), the motion detector and timer switch transmit a signal to the electrical braking component to enable motion of the at least one caster wheel and to deactivate the at least one ultraviolet (UV) light emitting diode (LED).

The present disclosure relates also to a method of mounting a lighting assembly that includes: providing at least one enclosure defining an internal volume configured and disposed to receive in the internal volume a portion of at least one caster wheel that includes a rotatable shaft enabling rotation of the one or more caster wheels; attaching via at least one structural mounting member the one or more enclosures to the rotatable shaft; and disposing at least one of at least one ultraviolet (UV) light-emitting diode (LED) in the internal volume of the one or more enclosures to interface the portion of the one or more caster wheels thereby enabling UV light emitting from the LED to illuminate the portion of the one or more caster wheels to enable sterilization of pathogens colonizing at least a portion of the portion of the one or more caster wheels received in the internal volume and to at least partially illuminate ambient surroundings, wherein the steps of providing at least one enclosure, attaching the enclosure to the rotatable shaft and disposing the at least one UV LED in the internal volume of the one or more enclosures define thereby a method of mounting a caster enclosure and UV LED sterilization and illumination lighting assembly, or of disposing at least one LED on an external surface of the one or more enclosures to at least partially illuminate ambient surroundings, wherein the steps of providing the one or more enclosures, disposing the one or more LED on an external surface of the one or more enclosures, and attaching via at least one structural mounting member the one or more enclosures to the rotatable shaft define thereby a method of mounting an LED illumination lighting assembly, or combinations of the steps of providing at least one enclosure, attaching the one or more enclosures to the rotatable shaft and disposing the one or more UV LEDs in the internal volume of the one or more enclosures defining thereby a method of mounting a caster enclosure and UV LED sterilization and illumination lighting assembly and of providing the one or more enclosures, disposing the one or more LEDs on an external surface of the one or more enclosures, and attaching via at least one structural mounting member the one or more enclosures to the rotatable shaft defining thereby a method of mounting an LED illumination lighting assembly.

In an aspect, the method of mounting a lighting assembly further includes: mounting a power supply such that the power supply is in electrical communication with the one or more UV LEDs of the caster enclosure and UV LED sterilization and illumination lighting assembly or with the one or more LEDs of the caster enclosure and LED illumination lighting assembly or combinations thereof.

In an aspect, the method of mounting a lighting assembly further includes: providing a motion detector and timer switch; and an electrical braking component configured to enable braking of the one or more caster wheels; and disposing on a surface of the swivel frame an electrical power supply in electrical communication with the motion detector and timer switch and the electrical braking component and with the one or more LEDs, wherein the one or more LEDs disposed on a surface of the swivel frame is at least one ultraviolet (UV) light emitting diode (LED) disposed on the surface of the swivel frame to interface a portion of the one or more caster wheels thereby enabling UV light emitting from the LED to illuminate the portion of the one or more caster wheels to enable sterilization of pathogens colonizing at least the portion of the one or more caster wheels; wherein, upon a predetermined time of motion or distance of motion of the caster wheel assembly, the motion detector and timer switch transmit a signal to the electrical braking component to brake motion of the caster wheel assembly and to electrically activate the one or more ultraviolet (UV) light emitting diodes (LED) to illuminate the portion of the one or more caster wheels to enable sterilization of pathogens colonizing at least the portion of the one or more caster wheels.

In an aspect, the method of mounting a lighting assembly includes, wherein upon expiration of a predetermined activation time of at least one ultraviolet (UV) light emitting diode (LED), the motion detector and timer switch transmit a signal to the electrical braking component to enable motion of the one or more caster wheels and to deactivate the one or more ultraviolet (UV) light emitting diodes (LED).

The present disclosure also relates to a method of mounting a light emitting diode (LED) that includes providing a caster wheel assembly having a swivel frame; and disposing on a surface of the swivel frame at least one LED to at least partially illuminate ambient surroundings.

In an aspect, the method of mounting a light emitting diode (LED) includes wherein the disposing on a surface of the swivel frame at least one LED to at least partially illuminate ambient surroundings includes disposing at least one ultraviolet (UV) light emitting diode (LED) on the surface of the swivel frame to interface a portion of at least one caster wheel of the caster wheel assembly thereby enabling UV light emitting from the LED to illuminate the portion of the one or more caster wheels to enable sterilization of pathogens colonizing at least the portion of the one or more caster wheels and to at least partially illuminate ambient surroundings.

In an aspect, the method of mounting a light emitting diode (LED) includes wherein the disposing on a surface of the swivel frame at least one LED to at least partially illuminate ambient surroundings includes disposing the one or more LEDs on an external surface of the swivel frame to at least partially illuminate ambient surroundings.

In an aspect, the method of mounting a light emitting diode (LED) further includes mounting a power supply to the caster wheel assembly such that the power supply is in electrical communication with the one or more LEDs.

In an aspect, the method of mounting a light emitting diode (LED) further includes providing a motion detector and timer switch; and an electrical braking component configured to enable braking of, or halting motion of, at least one caster wheel of the caster wheel assembly; and disposing on a surface of the caster wheel assembly an electrical power supply in electrical communication with the motion detector and timer switch and the electrical braking component and with the one or more LEDs, wherein the one or more LEDs disposed on a surface of the swivel frame is at least one ultraviolet (UV) light emitting diode (LED) disposed on the surface of the swivel frame to interface a portion of at least one caster wheel of the caster wheel assembly thereby enabling UV light emitting from the LED to illuminate the portion of the caster wheel to enable sterilization of pathogens colonizing at least the portion of the one or more caster wheels; wherein, upon a predetermined time of motion or distance of motion of the caster wheel assembly, the motion detector and timer switch transmit a signal to the electrical braking component to brake motion of the caster wheel assembly and to electrically activate the one or more ultraviolet (UV) light emitting diodes (LED) to illuminate the portion of the one or more caster wheels to enable sterilization of pathogens colonizing at least the portion of the one or more caster wheels.

In an aspect, the method of mounting a light emitting diode (LED) includes wherein upon expiration of a predetermined activation time of at least one ultraviolet (UV) light emitting diode (LED), the motion detector and timer switch transmit a signal to the electrical braking component to enable motion of the one or more caster wheels and to deactivate the at least one ultraviolet (UV) light emitting diode (LED).

In each of the foregoing embodiments and/or aspects, the electrical power supply may be selected from the group consisting of a battery, an ultracapacitor, an electrical generator, a photovoltaic cell, or a wall socket or combinations thereof.

The electrical power supply may be wirelessly rechargeable.

BRIEF DESCRIPTION OF THE DRAWINGS

The above-mentioned advantages and other advantages will become more apparent from the following detailed description of the various exemplary embodiments of the present disclosure with reference to the drawings wherein:

FIGS. 2A, 2B, 2C illustrate examples of polished zinc-plated soft tread swivel casters for hospital service;

FIGS. 10A and 10B illustrate the caster wheels of FIGS. 3A and 3B, respectively, that have been modified as caster wheel and sterilization lighting assemblies that include UV LEDs mounted under casters to illuminate wheels that rotate on axles;

DETAILED DESCRIPTION

The word "exemplary" is used herein to mean "serving as an example, instance, or illustration." Any embodiment described herein as "exemplary" is not necessarily to be construed as preferred or advantageous over other embodiments.

It is to be understood that the method steps described herein need not necessarily be performed in the order as described. Further, words such as "thereafter," "then," "next," etc., are not intended to limit the order of the steps. Such words are simply used to guide the reader through the description of the method steps.

The present disclosure relates to lighting assemblies that includes ultra-violet (UV) light-emitting diodes (LEDs) mounted on inner surfaces of enclosures that are configured and disposed to interface with the rolling surfaces of one or more caster wheels.

In embodiments, a lighting assembly according to the present disclosure is configured and disposed to be mounted on commercially available casters, for example, such as those supplied by Service Caster Corporation (West Reading, Pa. USA). See the following website:

http://shop.servicecaster.com/medical-hospital-casters-s/2036.htm?gclid=CMuPp8XfjdlCFZiCswod3iUOvQ Those skilled in the art will recognize that other designs of casters not explicitly illustrated in the present disclosure may be subjected to mounting of the sterilization lighting assemblies described herein and fall within the scope of the present disclosure.

FIGS. 1-5 illustrate various types of caster wheels that are utilized in the type of facilities described wherein the spread of viruses, bacteria and pathogens is of particular concern.

Figure 1:
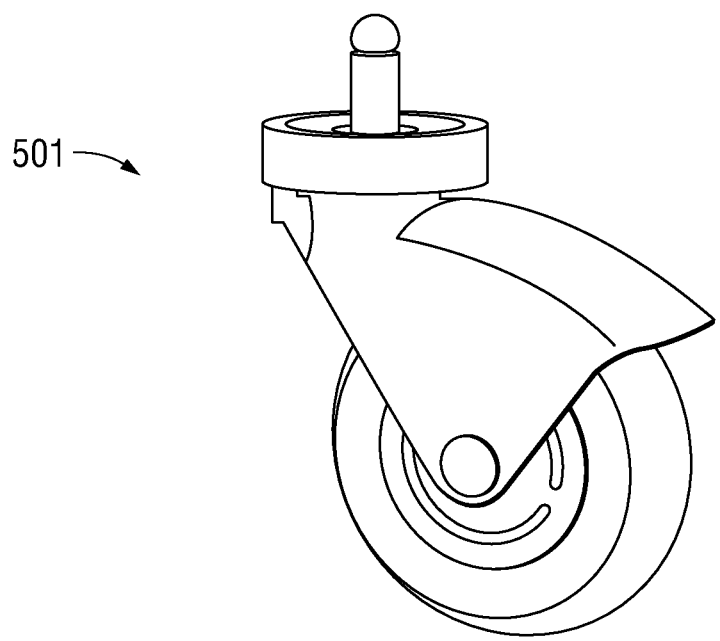
FIG. 1 illustrates a single wheel soft tread type swiveling caster.

FIG. 1 illustrates a single wheel soft tread type swiveling caster 501.

FIGS. 2A-2C illustrate examples of polished zinc-plated soft tread swivel casters 502A, 502B and 502C, respectively, for hospital service.

Figure 3A:
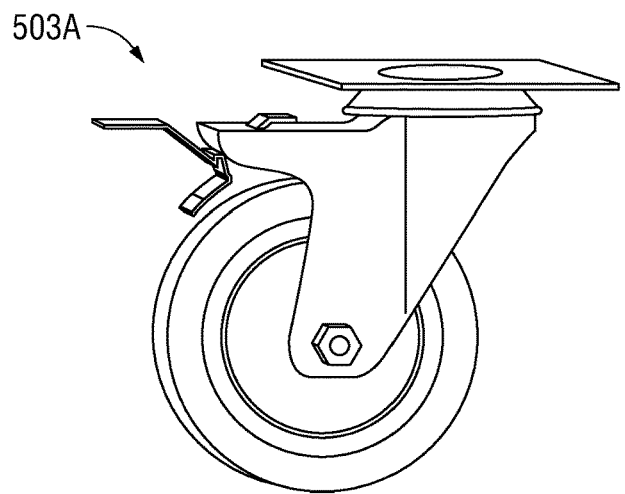
FIGS. 3A-3B illustrate examples of stainless steel soft tread swivel casters.
Figure 3B:
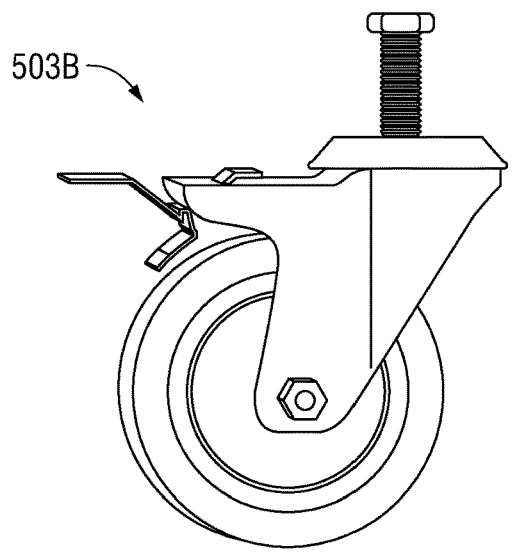

FIGS. 3A-3B illustrate examples of stainless steel soft tread swivel casters 503A and 503B, respectively.

Figure 4A:
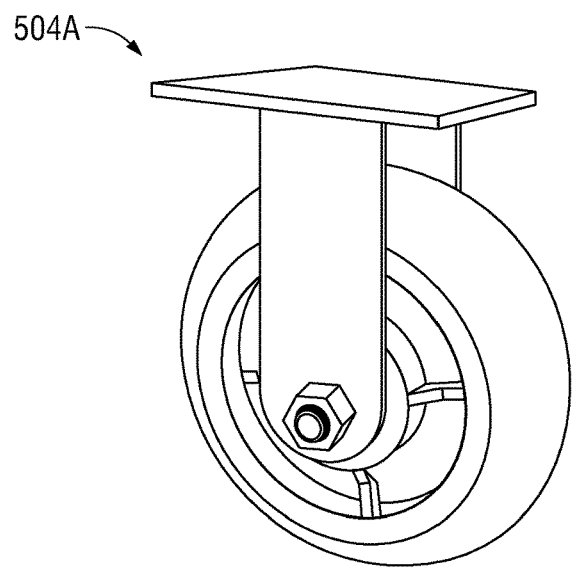
FIGS. 4A-4B illustrate examples of heavy duty top plate hospital and medical soft tread swivel casters.
Figure 4B:
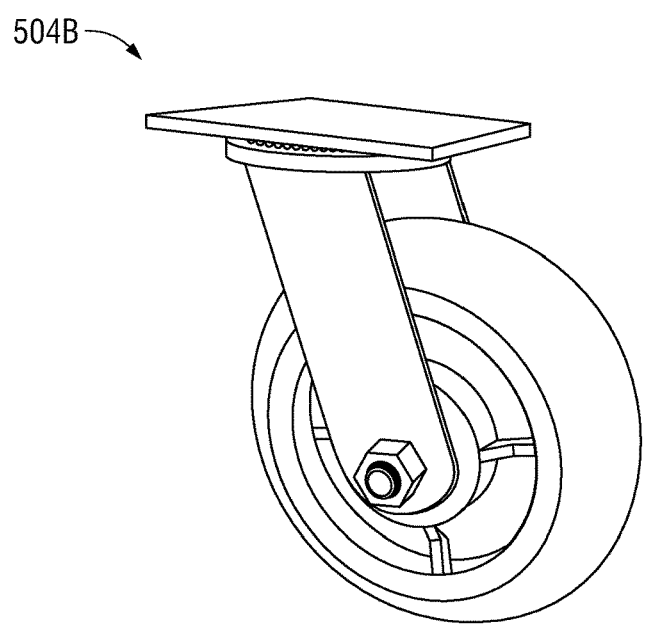

FIGS. 4A-4B illustrate examples of heavy duty top plate hospital and medical soft tread swivel casters 504A and 504B, respectively.

Figure 5:
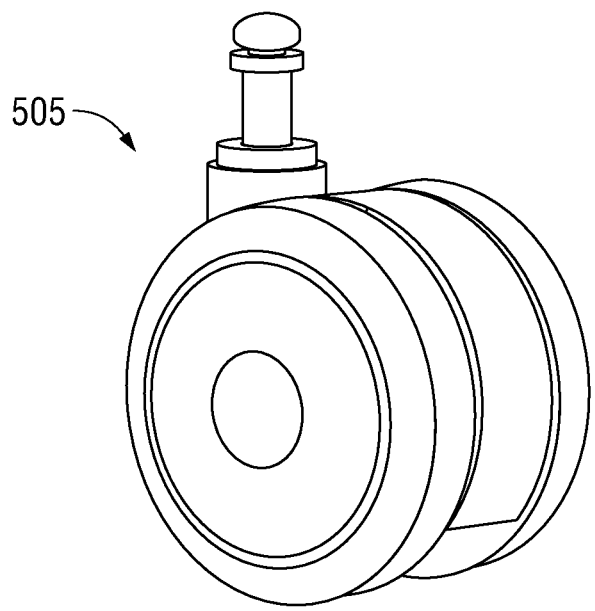
FIG. 5 illustrates an example of a twin wheel soft tread swivel caster for hospitals and medical facilities.

FIG. 5 illustrates an example of a twin wheel soft tread swivel caster 505 for hospitals and medical facilities.

Figure 6:
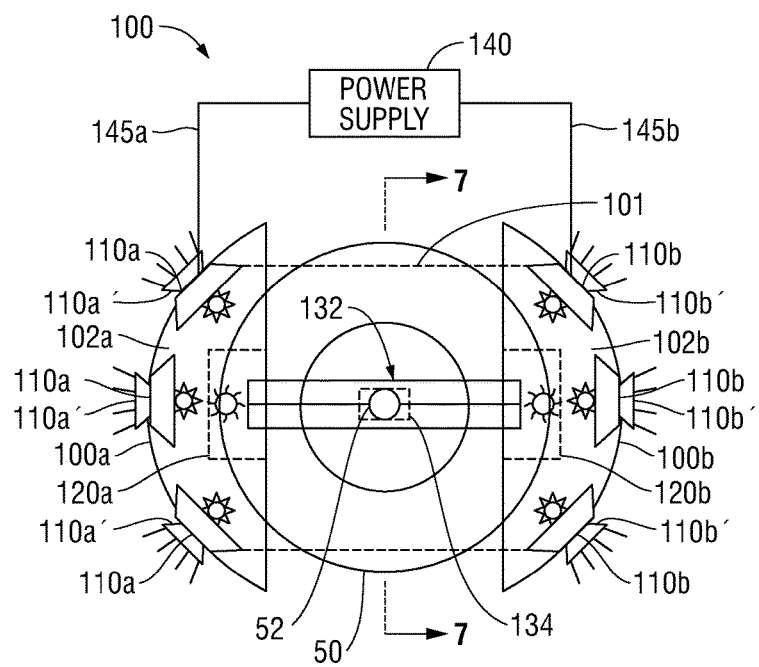
FIG. 6 illustrates a side view of an attachable and removable caster enclosure and UV LED lighting assembly according to the present disclosure that is mounted on a caster representing one of the casters of FIGS. 1-5.

FIG. 6 illustrates a side view of an attachable and removable caster enclosure and UV LED lighting assembly according to the present disclosure that is mounted on a caster representing one of the casters of FIGS. 1-5.

Figure 7:
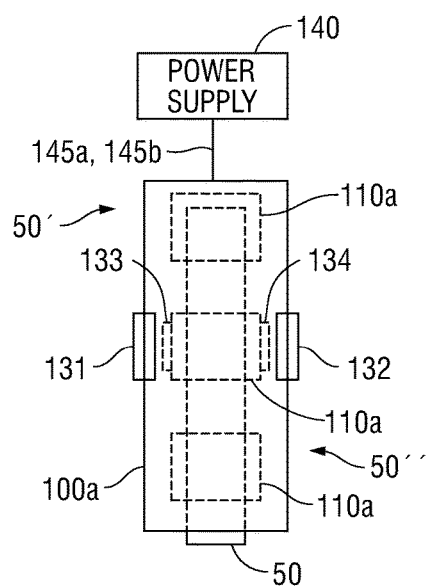
FIG. 7 illustrates an end view of the UV LED caster enclosure assembly that is mounted on a caster taken along section line 7-7 of FIG. 6.

FIG. 7 illustrates an end view of the UV LED caster enclosure assembly that is mounted on a caster taken along section line 7-7 of FIG. 6.

Figure 8:
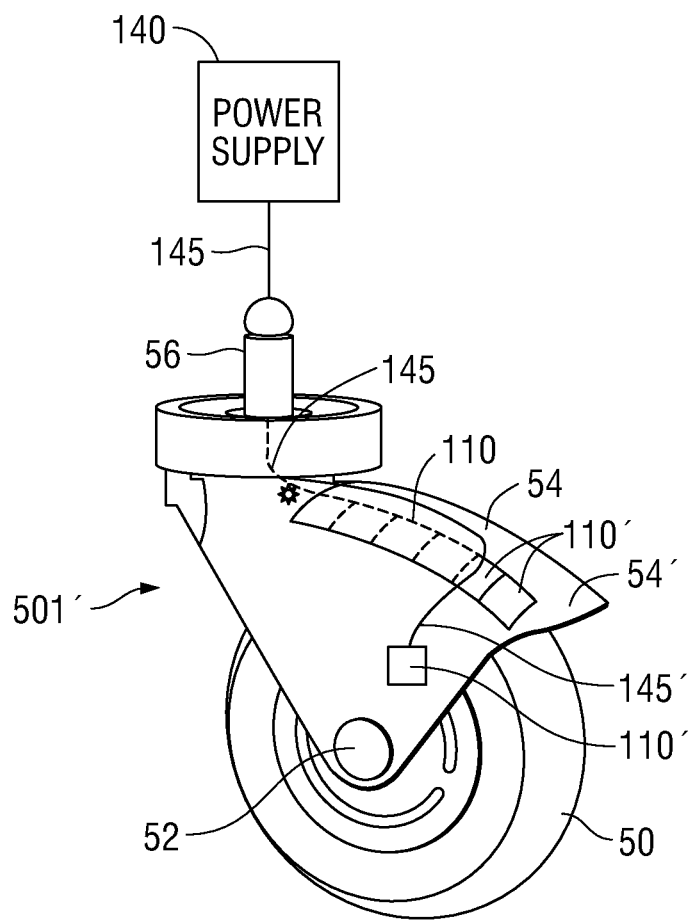
FIG. 8 illustrates the caster wheel of FIG. 1 that has been modified as a caster wheel and sterilization lighting assembly that includes UV LEDs mounted under the caster to illuminate the wheel that rotates on an axle.

FIG. 8 illustrates the caster wheel 501 of FIG. 1 that has been modified as a caster wheel and sterilization lighting assembly 501' that includes UV LEDs 110 mounted under swivel frame or caster 54 to illuminate wheel 50 that rotates on axle 52.

More particularly, referring to FIGS. 6 and 7, a sterilization lighting assembly 100 according to embodiments of the present disclosure includes at least one enclosure or housing 100a and/or 100b defining an internal volume 102a and/or 102b that is configured and disposed to receive in the internal volume 102a and/or 102b, a portion of at least one caster wheel 50 that includes a rotatable shaft 52 enabling rotation of the at least one caster wheel 50, respectively. At least one structural mounting member, e.g., cross-brace 131 and/or 132, is (are) configured and disposed to attach the at least one chord-shaped enclosure or housing 100a and/or 100b to the rotatable shaft 52.

In an aspect of the present disclosure, the enclosure or housing 100a and/or 100b may be chord-shaped which is illustrated in FIGS. 6-7 by way of example, and will be described herein as such. Other shapes of the enclosure or housing 100a and/or 100b may include rectangular or multilateral, e.g., semi-hexagon or semi-octagon, etc.

The sterilization lighting assembly 100 further includes at least one ultraviolet (UV) light-emitting diode (LED) 110a and/or 110b disposed in the internal volume 102a and/or 102b of the at least one chord-shaped enclosure 100a and/or 100b to interface the portion of the at least one caster wheel 50 thereby enabling UV light emitting from the LED or additional UV LEDs 110a and/or 110b disposed along the internal surfaces defined by the at least one chord-shaped enclosure 100a and/or 100b to illuminate the portion of the at least one caster wheel 50 to enable sterilization of pathogens colonizing at least a portion of the portion of the at least one caster wheel 50 received in the internal volume 102a and/or 102b.

The at least one chord-shaped enclosure 100a and/or 100b, the at least one structural mounting member, e.g., cross-brace 131 and/or 132, and the at least one UV LED or additional UV LEDs 110a and/or 110b define thereby a caster enclosure and UV LED sterilization lighting assembly 100 according to embodiments of the present disclosure.

FIG. 6 further discloses additional UV LEDs 120a that may be mounted within the internal volume 102a of UV LED enclosure or housing 100a and UV LEDs 120b mounted within internal volume 102b of UV LED enclosure or housing 100b that are configured and disposed to illuminate the side surfaces of the caster wheel or wheels 50.

Additionally, an extended height enclosure 101 may be provided which further encloses the side surfaces of caster wheel or wheels 50 and which further join the UV LED housings or enclosures 100a and 100b.

FIG. 7 further discloses cross-braces 132 are mounted on side 50" of caster wheel or wheels 50 and cross-braces 131 are mounted on side 50' of the caster wheel or wheels 50.

The cross-braces 131 are mounted to the caster wheel rotating shaft 52 on side 50' via a cross-brace joint 133 that enables rotation of the shaft 52 and thereby the caster wheel 50. Similarly, cross-braces 132 are mounted to the caster wheel rotating shaft 52 on side 50" via a cross-brace joint 134 that also enables rotation of the shaft 52 and thereby the caster wheel 50.

The foregoing describes some of the numerous ways and variations of how the enclosures could be mounted to enable the UV LEDs to radiate the UV light onto the different surfaces of the wheel.

It should be realized that the UV LEDs 110a and 110b inherently provide at least partial illumination to the ambient surroundings. Furthermore, alternatively, or in addition, illumination LEDs 110a' and 110b' may be mounted on the exterior surface of chord-shaped enclosures 100a and 100b, respectively, and may be in electrically communication with power supply 140 through wiring 145a directed to the at least one LED 110a' and through wiring 145b directed to the at least one LED 110b' thereby providing at least partial illumination to the ambient surroundings.

The enclosures 100a and 100b can be made from microbial resistant materials and titanium dioxide nanoparticles can be applied to the surfaces of caster wheel or wheels 50 to enhance sterilization:

See for example: T. Y. Kim et al., "(320aK) Sterilization of Pathogenic Bacteria Using Titanium Dioxide Photocatalyst", AIChE Annual Meeting, 2006.

Power Supply 140 is in electrical communication with the UV LEDs 110a and 110b through wiring 145a directed to the at least one UV LED 110a and through wiring 145b directed to the at least one UV LED 110b may be a dedicated rechargeable battery pack or one or more ultracapacitors mounted on the caster enclosures 100a or 100b or on the equipment being transported or power can be generated by electromagnetic induction from rotation of the casters themselves, etc. Alternatively, the UV LEDs 110 may include self-contained wirelessly rechargeable power supplies (not shown). In addition, one or more photovoltaic cells that capture indoor lighting could be used either directly or to charge batteries in the power supply 140 while the cart or equipment mounted on the caster wheels 501 to 505 is stationary.

Alternatively, or in addition thereto, the power supply 140 may be supplied power for recharging via an extension cord (not shown) connected to a conventional electrical wall socket (not shown) in the vicinity of the sterilization lighting assembly 100. Further, the power supply 140 may be the conventional electrical wall socket in the vicinity of the sterilization lighting assembly 100 to which an extension cord (not shown) is connected.

The foregoing aspects of power supply 140 may be utilized individually or in combination.

FIG. 8 illustrates the caster wheel 501 of FIG. 1 that has been modified as a caster wheel and sterilization lighting assembly 501' that includes UV LEDs 110 mounted under swivel frame or caster 54 to illuminate wheel 50 that rotates on axle 52. The UV LEDs 110 are supplied electrical power in a similar manner as described above with respect to FIGS. 6 and 7 via power supply 140 and power cord(s) 145 through or via a caster swivel shaft 56. Alternatively, the UV LEDs 110 may include self-contained wirelessly rechargeable power supplies (not shown). In addition, one or more photovoltaic cells that capture indoor lighting could be used either directly or to charge batteries in the power supply 140 while the cart or equipment mounted on the caster wheels 501' is stationary.

In addition, or alternatively, one or more illumination LEDs 110' may be mounted on an external surface 54' of swivel frame or caster 54 and may be electrically coupled to power supply 140 via power cords 145 and/or 145', thereby enabling the caster wheel 50 to provide at least partial illumination to the ambient surroundings. The power supply 140, power cords 145 and/or 145' and illumination LEDs 110' may be made water-proof to militate against flooding conditions that may be encountered.

Figure 9B:
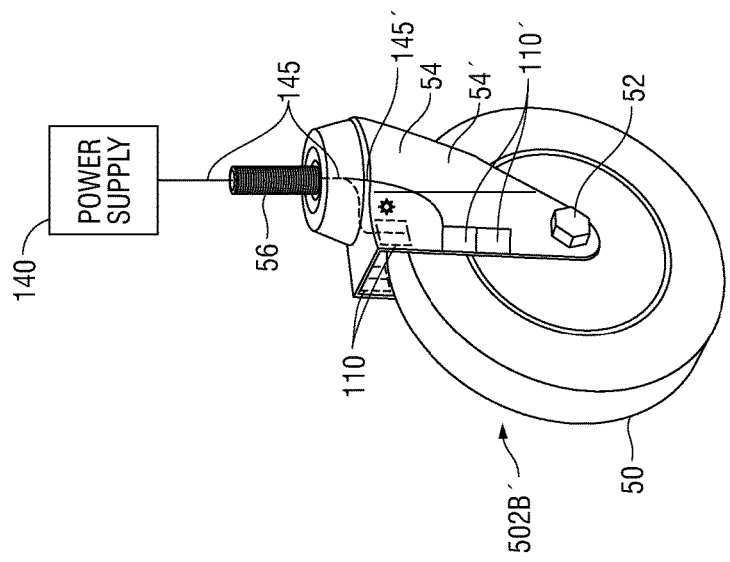
FIGS. 9A, 9B and 9C illustrate the caster wheels of FIGS. 2A, 2B and 2C, respectively, that have been modified as caster wheel and sterilization lighting assemblies that include UV LEDs mounted under the casters to illuminate the wheels that rotate on axles.
Figure 9A:
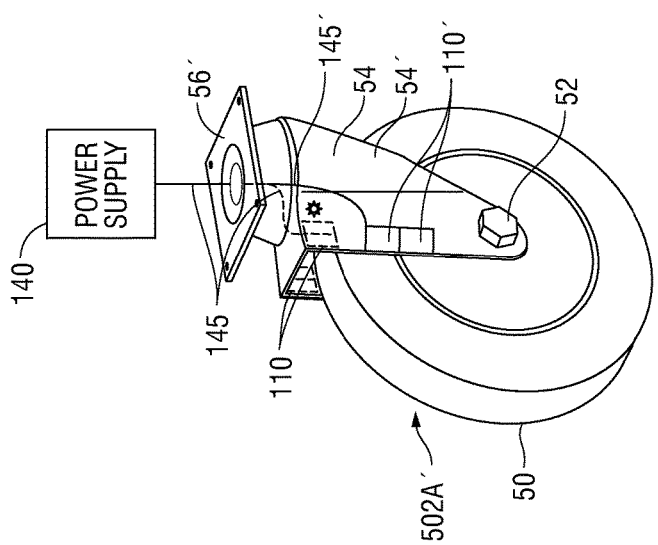
Figure 9C:
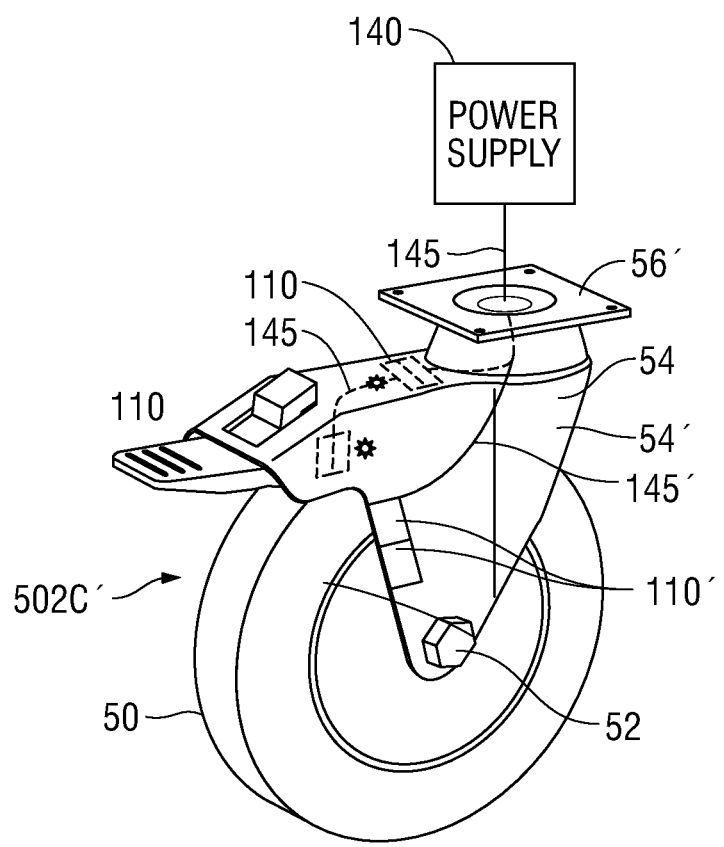

FIGS. 9A, 9B and 9C illustrate the caster wheels 502A, 502B and 502C of FIGS. 2A, 2B and 2C that have been modified as caster wheel and sterilization lighting assemblies 502A', 502B' and 502C', respectively, that include UV LEDs 110 mounted under casters 54 to illuminate wheels 50 that rotate on axle 52. Again, the UV LEDs 110 are supplied electrical power in a similar manner as described above with respect to FIGS. 6 and 7 via power supply 140 and power cord(s) 145 through or via caster wheel swivel shaft receptacle 56' (502A' in FIG. 9A or 502C' in FIG. 9C) or caster swivel shaft 56 (502B' in FIG. 9B). Alternatively, again, the UV LEDs 110 may include self-contained wirelessly rechargeable power supplies (not shown). In addition, one or more photovoltaic cells that capture indoor lighting could be used either directly or to charge batteries in the power supply 140 while the cart or equipment mounted on the caster wheels 502A', 502B' or 502C' is stationary.

In a similar manner as with respect to FIG. 8, in addition, or alternatively, one or more illumination LEDs 110' may be mounted on an external surface 54' of swivel frame or caster 54 of caster wheels 50 as illustrated in FIGS. 9A, 9B and 9C and may be electrically coupled to power supply 140 via power cords 145 and/or 145', thereby enabling the caster wheel 50 to provide at least partial illumination to the ambient surroundings. The power supply 140, power cords 145 and/or 145' and illumination LEDs 110' may be made water-proof to mitigate against flooding conditions that may be encountered.

FIGS. 10A and 10B illustrate the caster wheels 503A and 503B of FIGS. 3A and 3B that have been modified as caster wheel and sterilization lighting assemblies 503A' and 503B', respectively, that include UV LEDs 110 mounted under casters 54 to illuminate wheels 50 that rotate on axle 52. Again, the UV LEDs 110 are supplied electrical power in a similar manner as described above with respect to FIGS. 6 and 7 via power supply 140 and power cord(s) 145 through or via caster wheel swivel shaft receptacle 56' (503A' in FIG. 10A) or caster swivel shaft 56 (503B' in FIG. 10B). Alternatively, again, the UV LEDs 110 may include self-contained wirelessly rechargeable power supplies (not shown). In addition, one or more photovoltaic cells that capture indoor lighting could be used either directly or to charge batteries in the power supply 140 while the cart or equipment mounted on the caster wheels 503A' or 503B' is stationary.

In a similar manner as with respect to FIGS. 9A, 9B and 9C, in addition, or alternatively, one or more illumination LEDs 110' may be mounted on an external surface 54' of swivel frame or caster 54 of caster wheels 50 as illustrated in FIGS. 10A and 10B and may be electrically coupled to power supply 140 via power cords 145 and/or 145', thereby enabling the caster wheel 50 to provide at least partial illumination to the ambient surroundings. The power supply 140, power cords 145 and/or 145' and illumination LEDs 110' may be made water-proof to mitigate against flooding conditions that may be encountered.

Figure 11B:
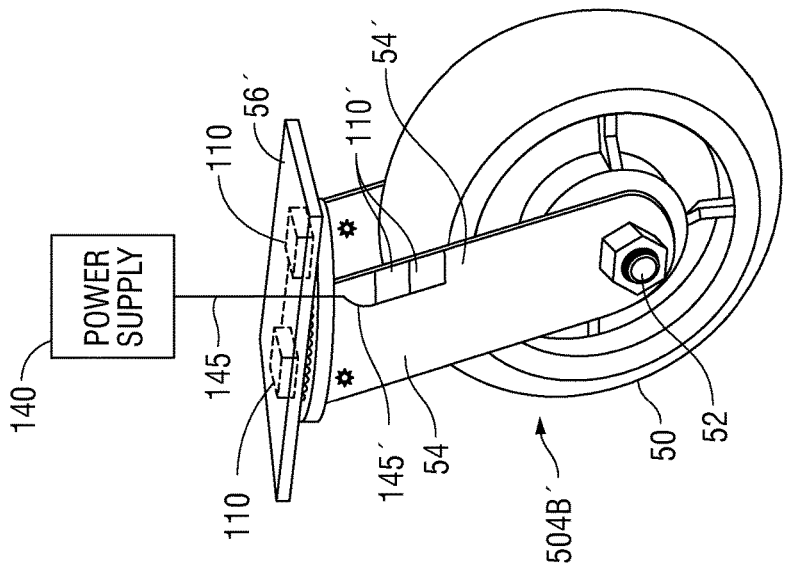
FIGS. 11A and 11B illustrate the caster wheels of FIGS. 4A and 4B, respectively, that have been modified as caster wheel and sterilization lighting assemblies that include UV LEDs mounted under casters to illuminate wheels that rotate on an axle.
Figure 11A:
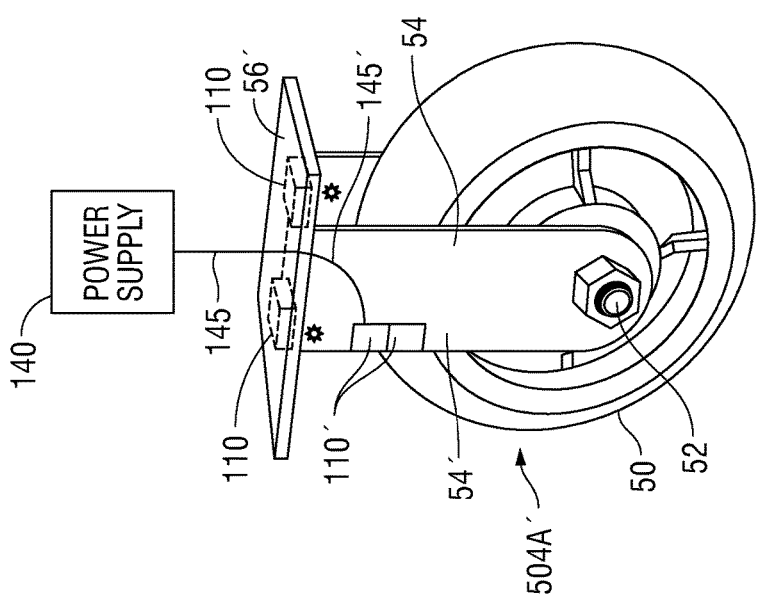
Figure 12:
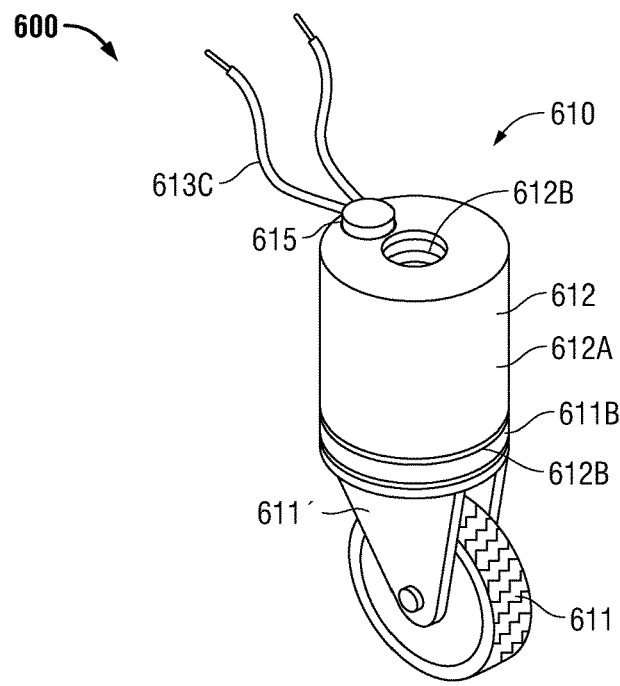
FIG. 12 illustrates an isometric view of another aspect of the present disclosure wherein a caster wheel assembly having an integrated electrical braking device further includes at least one UV LED for UV sterilization following braking of the caster wheel.
Figure 13:
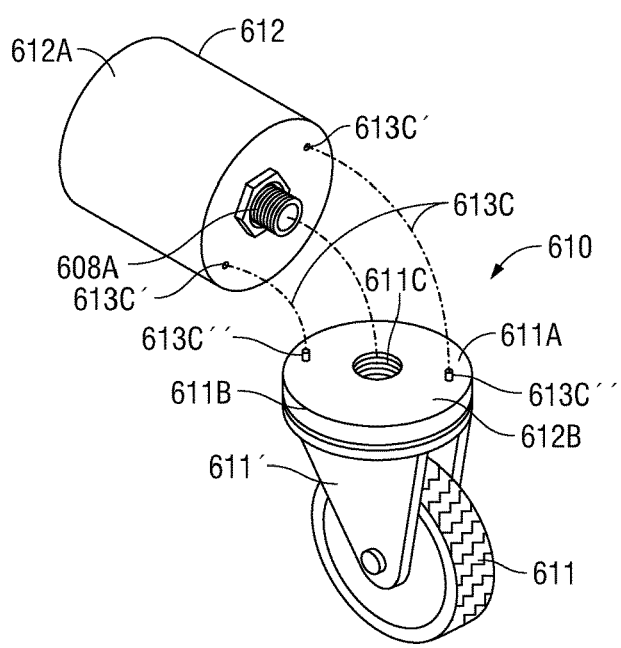
FIG. 13 illustrates an isometric view of the caster wheel assembly of FIG. 12 with the electronic braking component separated to reveal the bolt, which screws into the top surface of the caster wheel mounting bracket.
Figure 14:
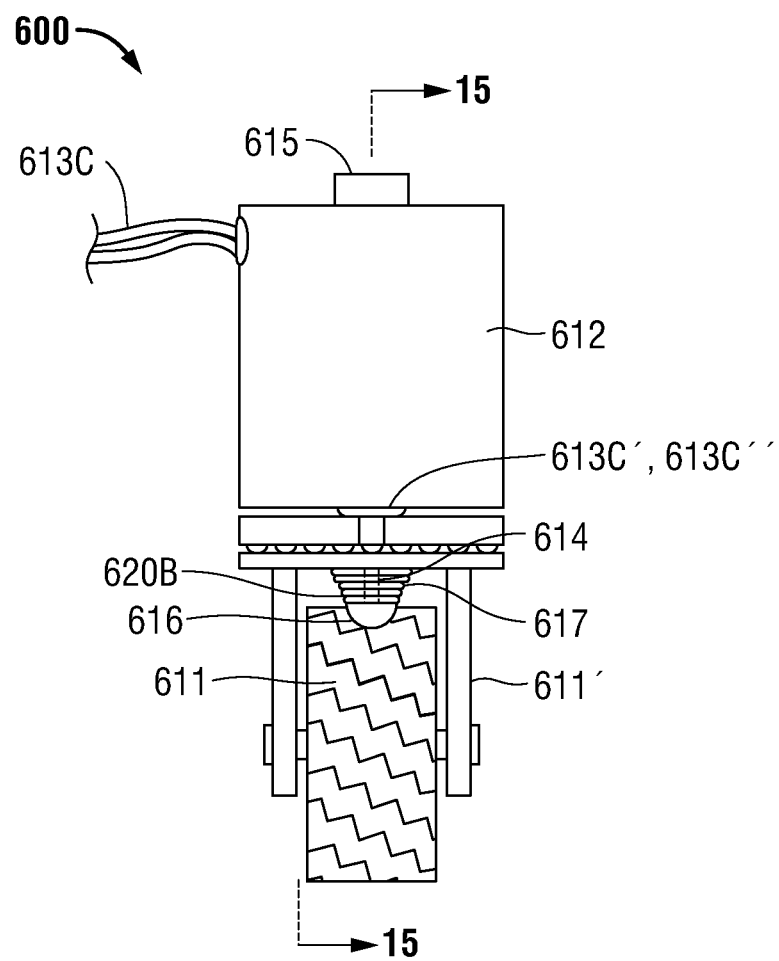
FIG. 14 illustrates a side view of the caster wheel assembly having an integrated electrical braking device.

FIGS. 11A and 11B illustrate the caster wheels 504A and 504B of FIGS. 4A and 4B that have been modified as caster wheel and sterilization lighting assemblies 504A' and 504B', respectively, that include UV LEDs 110 mounted under casters 54 to illuminate wheels 50 that rotate on axle 52. Again, the UV LEDs 110 are supplied electrical power in a similar manner as described above with respect to FIGS. 6 and 7 via power supply 140 and power cord(s) 145 through or via caster wheel swivel shaft receptacle 56' (504A' in FIG. 11A and 504B' in FIG. 11B). Alternatively, again, the UV LEDs 110 may include self-contained wirelessly rechargeable power supplies (not shown). In addition, one or more photovoltaic cells that capture indoor lighting could be used either directly or to charge batteries in the power supply 140 while the cart or equipment mounted on the caster wheels 504A' or 504B' is stationary.

Again, in a similar manner as with respect to FIGS. 10A and 10B, in addition, or alternatively, one or more illumination LEDs 110' may be mounted on an external surface 54' of swivel frame or caster 54 of caster wheels 50 as illustrated in FIGS. 11A and 11B and may be electrically coupled to power supply 140 via power cords 145 and/or 145', thereby enabling the caster wheel 50 to provide at least partial illumination to the ambient surroundings. The power supply 140, power cords 145 and/or 145' and illumination LEDs 110' may be made water-proof to mitigate against flooding conditions that may be encountered.

The UV LEDs 110a, 110b or 110 illustrated in FIGS. 6-11B may be activated for a desired adjustable period of time or adjustable distance traveled by the equipment to which the caster wheels 50 are mounted and can be set by a user via a power switch (not shown) or by a processor (not shown).

From the foregoing description of FIGS. 6-7, those skilled in the art will recognize that the present disclosure relates to a method of mounting sterilization lighting assembly 100 that includes the steps of providing at least one chord-shaped enclosure, e.g., 102a and/or 102b, defining an internal volume configured and disposed to receive in the internal volume a portion of at least one caster wheel 50 that includes rotatable shaft 52 enabling rotation of the caster wheel 50. The method includes attaching via at least one structural mounting member, e.g., 131 and/or 132, the at least one chord-shaped enclosure, e.g., 102a and/or 102b, to the rotatable shaft 52 and disposing at least one ultraviolet (UV) light-emitting diode (LED) 110a and/or 110b in the internal volume of the chord-shaped enclosure 102a/102b to interface the portion of the caster wheel 50 thereby enabling UV light emitting from the LED 110a and/or 110b to illuminate the portion of the caster wheel 50 to enable sterilization of pathogens colonizing at least a portion of the portion of the caster wheel 50 received in the internal volume.

The method includes providing the chord-shaped enclosure 102a and/or 102b, attaching the at least one structural mounting member 131 and/or 132 to the rotatable shaft 52 disposing at least one ultraviolet (UV) light-emitting diode (LED) 110a and/or 110b in the internal volume of the chord-shaped enclosure 102a/102b to interface the portion of the caster wheel 50 enables assembly thereby of a caster enclosure and UV LED sterilization lighting assembly.

The method may further include mounting power supply 140 to the caster wheel assembly 100 such that the power supply 140 is in electrical communication with the UV LED(s) 110*a* via wiring 145*a* and/or with the UV LED(s) 110*b* via wiring 145*b*.

The method may include mounting an electrical power supply 140 selected from the group consisting of a battery, an ultracapacitor, an electrical generator, a photovoltaic cell, or a wall socket or combinations thereof.

The mounting may include mounting an electrical power supply 140 that is wirelessly rechargeable.

From the foregoing description of FIGS. 8-11B, those skilled in the art will recognize and understand that in addition to the sterilization lighting assembly 100 described with respect to FIGS. 6 and 7, the present disclosure relates also to a caster wheel assembly, e.g., 501' in FIG. 8, 502A' in FIG. 9A, 502B' in FIG. 9B, 502C' in FIG. 9C, 503A' in FIG. 10A, 503B' in FIG. 10B, 504A' in FIG. 11A and 504B' in FIG. 11B, that includes a swivel frame or caster 54 configured to receive a caster wheel 50. The wheel 50 is rotatably coupled to the swivel frame or caster 54 via axle 52 to define thereby the caster wheel assembly. The swivel frame or caster 54 includes, or is configured to enable coupling to (e.g., caster wheel swivel shaft receptacle 56' in FIGS. 9A, 9C, 10A, 11A and 11B), rotatable shaft 56 enabling rotation of caster wheel 50 around the shaft 56.

The sterilization lighting assembly 100 further includes at least one ultraviolet (UV) light emitting diode (LED) 110 disposed on a surface of the swivel frame or caster 54 to interface a portion of the caster wheel 54 thereby enabling UV light emitting from the LED 110 to illuminate the portion of the caster wheel 50 to enable sterilization of pathogens colonizing at least the portion of the caster wheel.

Also from the foregoing description of FIGS. 8-11B, those skilled in the art will recognize and understand that the present disclosure relates also to a method of mounting an ultraviolet (UV) light emitting diode (LED) for sterilization of pathogens. The method includes providing a caster wheel assembly, e.g., 501', 502A', 502B', 502C', 503A', 503B', 504A' and 504B', having a swivel frame, e.g., swivel frame or caster 54, and mounting at least one UV LED 110 to the swivel frame or caster 54 to interface a portion of at least one caster wheel 50 of the caster wheel assembly 501' or 502A' thereby enabling UV light emitting from the one or more LEDs 110 to illuminate the portion of the caster wheel 50 to enable sterilization of pathogens colonizing at least the portion of the at least one caster wheel 50.

The method may further include mounting power supply 140 to the caster wheel assembly, e.g., 501', 502A', 502B', 502C', 503A', 503B', 504A' and 504B', such that the power supply 140 is in electrical communication with the UV LED(s) 110 via wiring 145.

The method may include mounting electrical power supply 140 selected from the group consisting of a battery, an ultracapacitor, an electrical generator, a photovoltaic cell, or a wall socket or combinations thereof.

The mounting may include mounting electrical power supply 140 that is wirelessly rechargeable.

In another aspect of the present disclosure, FIGS. 12-17 illustrate a caster wheel assembly 600 having an integrated electrical braking device 610 and further includes at least one UV LED, e.g., 620A and/or 620B for UV sterilization after the electrical braking device 610 receives a signal from motion detector and timer switch 615 to brake motion of at least one caster wheel 611 of the caster wheel assembly 600 to subject the surface of the caster wheel 611 to the UV sterilization provided by the UV LEDs 620A and/or 620B.

The electrical braking device 610 includes an electrical braking assembly 612 that is formed in an upper section 612A and a lower section 612B.

The upper section 612A includes a solenoid 613 that causes motion of a pin 614 that contacts the surface of the caster wheel 611 to effect braking of the caster wheel. The pin 614 passes through a bolt 608A along a bottom surface 613C' and a threaded opening 611C along a top surface 613C" of lower section 612B.

The solenoid 613 is electrically wired via wiring 613C to motion detector and timer switch 615, which is wired to a power supply 618.

The lower section 612B includes caster wheel 611 mounted to swivel frame 611' via a mounting bracket 611A, and a ball bearing 611B. The upper section 612A of electrical braking component 612 is secured to the lower section 612B and thereby to caster wheel 611 by screwing the bolt 608A of the upper section 612A of electrical braking component 612 into the threaded opening 611C on the mounting bracket 611A of lower section 612B.

The ball-bearing 611B is in rotatable contact with the mounting bracket 611A in the lower section 612B thereby enabling rotation of the swivel frame 611' and accordingly the caster wheel 611 to rotate about the mounting bracket 611A, which in turn enables rotation of the electrical braking component 612. The threaded opening 612B enables the electrical braking component 612 to be secured to the bottom surface of an object (not shown) for which the integrated electrical braking device 610 is being used in the same fashion as if the caster wheel 611 had been directly attached to the object.

The pin 614 attaches to a brake 616, which is positioned adjacent a spring 617 located on the bottom surface of the mounting bracket 611A. The spring 617 insures that a biasing force is placed upon the brake 616 as well as the pin 614. The spring 617 biases the pin upwards to ensure against unintentional braking of the caster wheel 611 when the solenoid 613 is not powered. However, it shall be noted that the total force output of the solenoid 613 must be sufficient to overcome the biasing force of the spring 617 in addition to a braking force required to successfully stop the caster wheel 611 via the brake 616.

The pin 614 attaches to the brake 616 via an attaching means comprising welding, bolting, screwing, molding, or adhesive or other suitable methods in the art. The pin 614 and the brake 616 are made of a material comprising metal, rubber, durable plastic, aramid fibers, carbon fibers, or wood.

As indicated above, the bottom surface of lower section 612B further includes at least one UV LED, e.g., 620A and/or 620B for UV sterilization after the electrical braking device 610 receives a signal from motion detector and timer switch 615 to brake motion of at least one caster wheel 611 of the caster wheel assembly 600 to subject the surface of the caster wheel 611 to the UV sterilization provided by the UV LEDs 620A and/or 620B.

More particularly, upon a predetermined time of motion or distance of motion of the caster wheel assembly 600, the motion detector and timer switch 615 transmits the signal to the electrical braking component 612 to halt motion of the caster wheel assembly 600 and to electrically activate at least one ultraviolet (UV) light emitting diode (LED), e.g., UV LEDs 620A and/or 620B, to illuminate the portion of the caster wheel 611 via UV beams 620UVa and 620UVb, respectively, to enable sterilization of pathogens colonizing at least the portion of the one or more caster wheels 611.

The magnitudes of the predetermined time of motion or distance of motion are each adjustable either by a user via the motion detection and timer switch 615 or by a processor (not shown) in communication with the motion detector and timer switch 615 that may be mounted on a cart or other equipment which is transportable via the caster wheel assembly 600.

Figure 15:
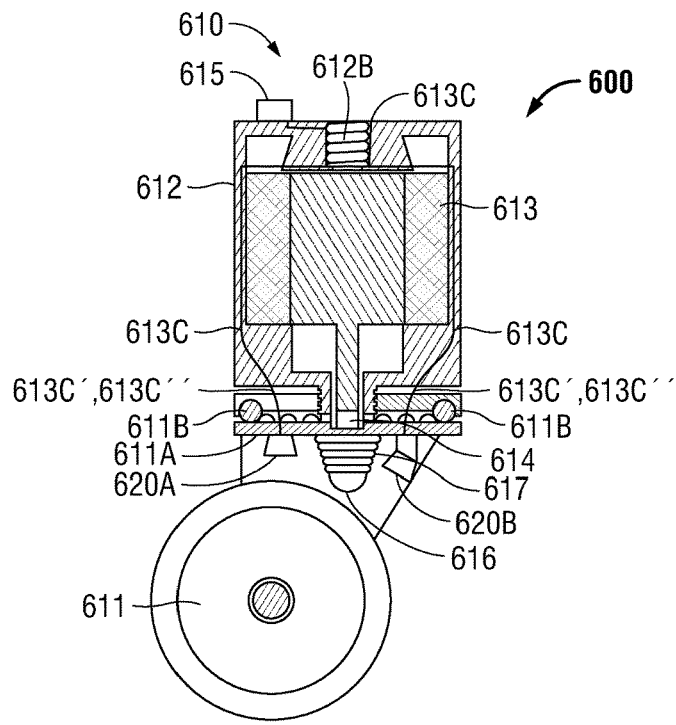
FIG. 15 illustrates a cross-sectional view of the caster wheel assembly of FIG. 14 with the electronic braking component along line 15-15 in FIG. 14 with the brake in the off position.
Figure 16:
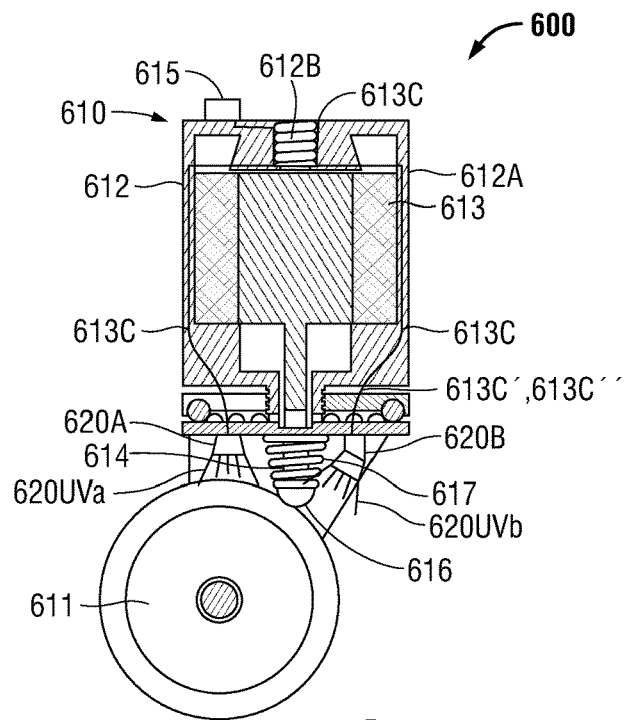
FIG. 16 illustrates a cross-sectional view of the caster wheel assembly of FIG. 14 with the electronic braking component along line 15-15 in FIG. 14 with the brake in the on position.
Figure 17:
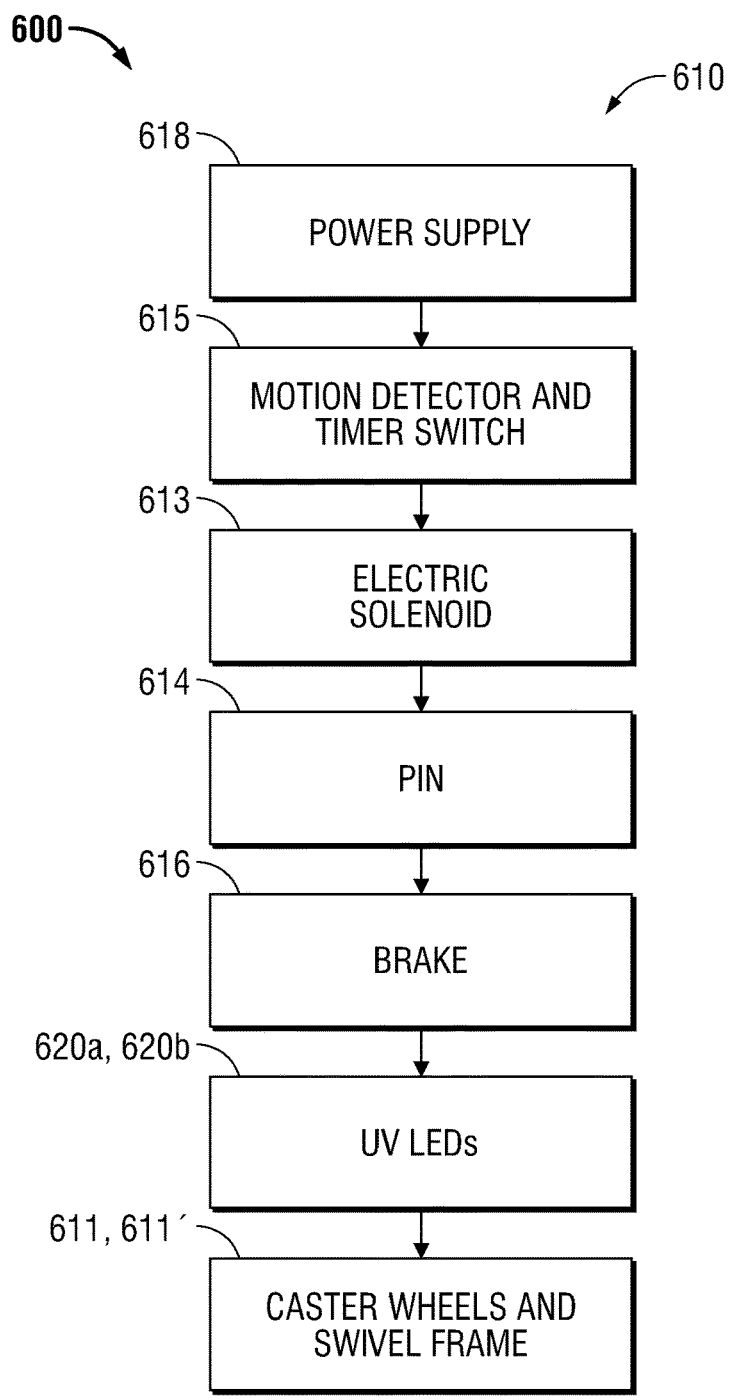
FIG. 17 illustrates a schematic block diagram of the various components of the caster wheel assembly having an integrated electrical braking device that further includes at least one UV LED for UV sterilization according to FIGS. 12-16.

Upon expiration of an adjustable predetermined activation time of at least one ultraviolet (UV) light emitting diode (LED), e.g., 620A and/or 620B, the motion detector and timer switch 615 transmits a signal to the electrical braking component 612 to enable motion of the one or more caster wheels 611, i.e., the electrical braking component 612 releases the one or more caster wheels 611, and to deactivate the one or more ultraviolet (UV) light emitting diodes (LED) e.g., 620A and/or 620B, As illustrated in FIGS. 15 and 16, the orientation of UV LED 620B may be at an angle with respect to the bottom surface of mounting bracket 611A to minimize distance from the UV LED 620B to the surface of the caster wheel 611.

The caster wheel assembly 600 having integrated electrical braking device 610 and respective components as described above with respect to FIGS. 12-17 may also be applied to the sterilization lighting assembly 100 that includes at least one enclosure or housing 100a and/or 100b as described above with respect to FIGS. 6-7.

The caster wheel assembly 600 having integrated electrical braking device 610 together with the UV LEDs 620A and/or 620B for UV sterilization together with the related components as described above may be adapted for all typical applications including caster wheels and may be integrated into either an existing caster wheel or part of a new caster wheel. Although the present disclosure has been described in considerable detail with reference to certain embodiments, other embodiments and versions are possible and contemplated. Therefore, the spirit and scope of the appended claims should not be limited to the description of the embodiments contained herein.

While several embodiments and methodologies of the present disclosure have been described and shown in the drawings, it is not intended that the present disclosure be limited thereto, as it is intended that the present disclosure be as broad in scope as the art will allow and that the specification be read likewise.

Therefore, the above description should not be construed as limiting, but merely as exemplifications of particular embodiments and methodologies. Those skilled in the art will envision other modifications within the scope of the claims appended hereto.

What is claimed is:

1. A lighting assembly comprising:
    at least one enclosure defining an internal volume configured and disposed to receive in the internal volume a portion of at least one caster wheel that includes a rotatable shaft enabling rotation of the at least one caster wheel;
    at least one structural mounting member configured and disposed to attach the at least one enclosure to the rotatable shaft; and
    one of at least one ultraviolet (UV) light-emitting diode (LED) disposed in the internal volume of the at least one enclosure to interface the portion of the at least one caster wheel thereby enabling UV light emitting from the LED to illuminate the portion of the at least one caster wheel to enable sterilization of pathogens colonizing at least a portion of the portion of the at least one caster wheel received in the internal volume and to at least partially illuminate ambient surroundings,
    the at least one enclosure, the at least one structural mounting member and the at least one UV LED defining thereby a caster enclosure and UV LED sterilization and illumination lighting assembly,
    or at least one LED disposed on an external surface of the at least one enclosure to at least partially illuminate ambient surroundings,
    the at least one enclosure, the at least one structural mounting member, and the at least one LED defining thereby a caster enclosure and LED illumination lighting assembly,
    or combinations of the at least one enclosure, the at least one structural mounting member and the at least one UV LED defining thereby a caster enclosure and UV LED sterilization and illumination lighting assembly and the at least one enclosure, the at least one structural mounting member, and the at least one LED defining thereby a caster enclosure and LED illumination lighting assembly.

2. The lighting assembly according to claim 1, further comprising:
    an electrical power supply in electrical communication with the at least one LED.

3. The lighting assembly according to claim 1, further comprising:
    a motion detector and timer switch;
    an electrical braking component configured to enable braking of the at least one caster wheel; and
    an electrical power supply in electrical communication with the motion detector and timer switch and the electrical braking component and with the at least one LED disposed on a surface of the at least one enclosure,
    wherein the at least one LED disposed on a surface of the at least one enclosure is
    at least one ultraviolet (UV) light emitting diode (LED) disposed on the surface of the at least one enclosure to interface a portion of the caster wheel thereby enabling UV light emitting from the LED to illuminate the portion of the caster wheel to enable sterilization of pathogens colonizing at least the portion of the at least one caster wheel;
    wherein, upon a predetermined time of motion or distance of motion of the caster wheel assembly, the motion detector and timer switch transmit a signal to the electrical braking component to halt motion of the caster wheel assembly and to electrically activate the at least one ultraviolet (UV) light emitting diode (LED) to illuminate the portion of the caster wheel to enable sterilization of pathogens colonizing at least the portion of the at least one caster wheel.

4. The lighting assembly according to claim 3, wherein upon expiration of a predetermined activation time of at least one ultraviolet (UV) light emitting diode (LED), the motion detector and timer switch transmit a signal to the electrical braking component to enable motion of the at least one caster wheel and to deactivate the at least one ultraviolet (UV) light emitting diode (LED).

5. A caster wheel assembly comprising:
    a swivel frame configured to receive at least one caster wheel;
    a wheel rotatably coupled to the swivel frame via an axle to define thereby a caster wheel assembly, the swivel frame including, or is configured to enable coupling to, a rotatable shaft enabling rotation of the at least one caster wheel; and at least one light emitting diode (LED) disposed on a surface of the swivel frame to at least partially illuminate ambient surroundings.

6. The caster wheel assembly according to claim 5, wherein the at least one LED disposed on a surface of the swivel frame is at least one ultraviolet (UV) light emitting diode (LED) disposed on the surface of the swivel frame to interface a portion of the caster wheel thereby enabling UV light emitting from the LED to illuminate the portion of the caster wheel to enable sterilization of pathogens colonizing at least the portion of the at least one caster wheel.

7. The caster wheel assembly according to claim 6, wherein the at least one light emitting diode (LED) is disposed on an external surface of the swivel frame to at least partially illuminate ambient surroundings.

8. The caster wheel assembly according to claim 5, further comprising:

an electrical power supply in electrical communication with the at least one LED.

9. The caster wheel assembly according to claim 6, further comprising:

a motion detector and timer switch;

an electrical braking component configured to enable braking of the caster wheel; and an electrical power supply in electrical communication with the motion detector and timer switch and the electrical braking component and with the at least one ultraviolet (UV) light emitting diode (LED) disposed on a surface of the swivel frame, wherein, upon a predetermined time of motion or distance of motion of the caster wheel assembly, the motion detector and timer switch transmit a signal to the electrical braking component to brake motion of the caster wheel assembly and to electrically activate the at least one ultraviolet (UV) light emitting diode (LED) to illuminate the portion of the caster wheel to enable sterilization of pathogens colonizing at least the portion of the at least one caster wheel.

10. The caster wheel assembly according to claim 9, wherein upon expiration of a predetermined activation time of at least one ultraviolet (UV) light emitting diode (LED), the motion detector and timer switch transmit a signal to the electrical braking component to enable motion of the at least one caster wheel and to deactivate the at least one ultraviolet (UV) light emitting diode (LED).

11. A method of mounting a lighting assembly, comprising:

providing at least one enclosure defining an internal volume configured and disposed to receive in the internal volume a portion of at least one caster wheel that includes a rotatable shaft enabling rotation of the at least one caster wheel;

attaching via at least one structural mounting member the at least one enclosure to the rotatable shaft; and disposing at least one of at least one ultraviolet (UV) light-emitting diode (LED) in the internal volume of the at least one enclosure to interface the portion of the at least one caster wheel thereby enabling UV light emitting from the LED to illuminate the portion of the at least one caster wheel to enable sterilization of pathogens colonizing at least a portion of the portion of the at least one caster wheel received in the internal volume and to at least partially illuminate ambient surroundings, the steps of providing at least one enclosure, attaching the enclosure to the rotatable shaft and disposing the at least one UV LED in the internal volume of the at least one enclosure defining thereby a method of mounting a caster enclosure and UV LED sterilization and illumination lighting assembly, or of disposing at least one LED on an external surface of the at least one enclosure to at least partially illuminate ambient surroundings, the steps of providing the at least one enclosure, disposing the at least one LED on an external surface of the at least one enclosure, and attaching via at least one structural mounting member the at least one enclosure to the rotatable shaft defining thereby a method of mounting an LED illumination lighting assembly, or combinations of the steps of providing at least one enclosure, attaching the enclosure to the rotatable shaft and disposing the at least one UV LED in the internal volume of the at least one enclosure enabling thereby a method of mounting a caster enclosure and UV LED sterilization and illumination lighting assembly and of providing the at least one enclosure, disposing the at least one LED on an external surface of the at least one enclosure, and attaching via at least one structural mounting member the at least one enclosure to the rotatable shaft defining thereby a method of mounting an LED illumination lighting assembly.

12. The method of mounting a lighting assembly according to claim 11, further comprising:

mounting a power supply such that the power supply is in electrical communication with the at least one UV LED of the caster enclosure and UV LED sterilization and illumination lighting assembly or with the at least one LED of the caster enclosure and LED illumination lighting assembly or combinations thereof.

13. The method of mounting a lighting assembly according to claim 12, further comprising:

providing a motion detector and timer switch; and an electrical braking component configured to enable braking of the at least one caster wheel; and disposing on a surface of the caster enclosure an electrical power supply in electrical communication with the motion detector and timer switch and the electrical braking component and with the at least one LED, wherein the at least one LED disposed on a surface of the caster enclosure is at least one ultraviolet (UV) light emitting diode (LED) disposed on the surface of the caster enclosure to interface a portion of the at least one caster wheel thereby enabling UV light emitting from the LED to illuminate the portion of the at least one caster wheel to enable sterilization of pathogens colonizing at least the portion of the at least one caster wheel;

wherein, upon a predetermined time of motion or distance of motion of the caster wheel assembly, the motion detector and timer switch transmit a signal to the electrical braking component to brake motion of the caster wheel assembly and to electrically activate the at least one ultraviolet (UV) light emitting diode (LED) to illuminate the portion of the at least one caster wheel to enable sterilization of pathogens colonizing at least the portion of the at least one caster wheel.

14. The method of mounting a lighting assembly according to claim 13, wherein upon expiration of a predetermined activation time of at least one ultraviolet (UV) light emitting diode (LED), the motion detector and timer switch transmit a signal to the electrical braking component to enable motion of the at least one caster wheel and to deactivate the at least one ultraviolet (UV) light emitting diode (LED).

15. A method of mounting a light emitting diode (LED) comprising:
   providing a caster wheel assembly having a swivel frame; and
   disposing on a surface of the swivel frame at least one LED to at least partially illuminate ambient surroundings.

16. The method of mounting a light emitting diode (LED) according to claim 15, wherein the disposing on a surface of the swivel frame at least one LED to at least partially illuminate ambient surroundings includes
   disposing at least one ultraviolet (UV) light emitting diode (LED) on the surface of the swivel frame to interface a portion of at least one caster wheel of the caster wheel assembly thereby enabling UV light emitting from the LED to illuminate the portion of the at least one caster wheel to enable sterilization of pathogens colonizing at least the portion of the at least one caster wheel and to at least partially illuminate ambient surroundings.

17. The method of mounting a light emitting diode (LED) according to claim 15, wherein the disposing on a surface of the swivel frame at least one LED to at least partially illuminate ambient surroundings includes disposing the at least one LED on an external surface of the swivel frame to at least partially illuminate ambient surroundings.

18. The method of mounting a light emitting diode (LED) according to claim 15, further comprising:
   mounting a power supply to the caster wheel assembly such that the power supply is in electrical communication with the at least one LED.

19. The method of mounting a light emitting diode (LED) according to claim 18, further comprising:
   providing
      a motion detector and timer switch; and
      an electrical braking component configured to enable braking of at least one caster wheel of the caster wheel assembly; and
   disposing on a surface of the caster wheel assembly an electrical power supply in electrical communication with the motion detector and timer switch and the electrical braking component and with the at least one LED,
   wherein the at least one LED disposed on a surface of the swivel frame is
   at least one ultraviolet (UV) light emitting diode (LED) disposed on the surface of the swivel frame to interface a portion of at least one caster wheel of the caster wheel assembly thereby enabling UV light emitting from the LED to illuminate the portion of the caster wheel to enable sterilization of pathogens colonizing at least the portion of the at least one caster wheel;
   wherein, upon a predetermined time of motion or distance of motion of the caster wheel assembly, the motion detector and timer switch transmit a signal to the electrical braking component to brake motion of the caster wheel assembly and to electrically activate the at least one ultraviolet (UV) light emitting diode (LED) to illuminate the portion of the caster wheel to enable sterilization of pathogens colonizing at least the portion of the at least one caster wheel.

20. The method of mounting a light emitting diode (LED) according to claim 19, wherein upon expiration of a predetermined activation time of at least one ultraviolet (UV) light emitting diode (LED), the motion detector and timer switch transmit a signal to the electrical braking component to enable motion of the at least one caster wheel and to deactivate the at least one ultraviolet (UV) light emitting diode (LED).

* * * * *